United States Patent [19]

Merianos

[11] Patent Number: 5,242,684

[45] Date of Patent: Sep. 7, 1993

[54] ANTIMICROBIAL, LOW TOXICITY, NON-IRRITATING COMPOSITION COMPRISING A BLEND OF BIS-QUATERNARY AMMONIUM COMPOUNDS COPRECIPITATED WITH A COPOLYMER OF VINYLPYRROLIDONE AND AN ACRYLAMIDO OR VINYL QUATERNARY AMMONIUM MONOMER

[75] Inventor: John J. Merianos, Middletown, N.J.

[73] Assignee: ISP Investments Inc., Wilmington, Del.

[21] Appl. No.: 783,017

[22] Filed: Oct. 25, 1991

[51] Int. Cl.$^5$ .................... A61K 31/14; A61K 31/79; A61K 7/06; A61K 7/50

[52] U.S. Cl. ................. 424/78.07; 424/78.29; 424/409; 424/70; 424/501; 514/846; 524/252; 252/106; 252/174.23; 252/DIG. 2; 252/DIG. 5; 252/DIG. 13; 564/294; 564/295

[58] Field of Search ............. 424/78.24, 78.29, 78.07, 424/409, 70, 71, 486, 487; 514/846; 252/106, 174.23, DIG. 2, DIG. 5, DIG. 13; 564/294, 295

[56] References Cited

U.S. PATENT DOCUMENTS

| 2,194,906 | 3/1940 | Krzikalla et al. | 564/295 |
| 2,683,147 | 7/1954 | Girod | 564/294 |
| 3,079,436 | 2/1963 | Hwa | 564/295 |
| 5,085,860 | 2/1992 | Junino et al. | 424/72 |

FOREIGN PATENT DOCUMENTS 2198725  6/1988  United Kingdom .

OTHER PUBLICATIONS

J. J. Merianos, Quaternary Ammonium Antimicrobial Compounds, in Disinfectants, Sterilizors and Preservatives; S. Block, ed.; Ch. 13; (Lea and Febiger) 1991.

Primary Examiner—Thurman K. Page
Assistant Examiner—E. J. Webman
Attorney, Agent, or Firm—Walter Katz; Marilyn J. Maue; Joshua J. Ward

[57] ABSTRACT

An antimicrobial, low toxicity, non-irritating composition comprises a blend of several bis-quaternary ammonium compounds coprecipitated with a copolymer of vinylpyrrolidone and an acrylamido or vinyl quaternary ammonium monomer.

14 Claims, No Drawings

ANTIMICROBIAL, LOW TOXICITY, NON-IRRITATING COMPOSITION COMPRISING A BLEND OF BIS-QUATERNARY AMMONIUM COMPOUNDS COPRECIPITATED WITH A COPOLYMER OF VINYLPYRROLIDONE AND AN ACRYLAMIDO OR VINYL QUATERNARY AMMONIUM MONOMER

BACKGROUND OF THE INVENTION

1. Field of the Invention

This invention relates to antimicrobial compounds having low toxicity, excellent solubility in water, and low irritation to the user.

2. Description of the Prior Art

Bis-quaternary ammonium compounds, such as acrylic alkyleneoxylated bis-quaternary ammonium compounds, have been formulated into shampoo and cosmetic cleansing compounds as mildness additives for the detergents therein; see U.S. Pat. No. 4,110,263. However, for these and other applications, where effective antimicrobial properties are needed, it is desired to provide compositions including such compounds which show enhanced antimicrobial activity, as compared to the individual compounds therein, and which also exhibit low toxicity, high solubility in water, and, moreover, little or no skin irritation for the user.

Accordingly, it is an object of the present invention to provide a composition comprising (a) a blend of bis-quaternary ammonium compounds and (b) a copolymer of vinylpyrrolidone and an acrylamido or vinyl quaternary ammonium monomer, which composition exhibits high antimicrobial activity, low toxicity, is water-soluble, and does not irritate the skin.

These and other objects and features of the invention will be made apparent from the following description herein.

SUMMARY OF THE INVENTION

What is provided herein are antimicrobial compositions comprising:

(a) a blend of bis-quaternary ammonium compounds selected from those represented by the formula:

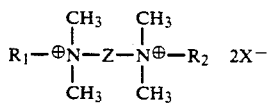

in which Z is $-(CH_2CH_2O)_nCH_2CH_2-$
where n is 1 or 2; or
$-CH_2CH=CH-CH_2-$; and
$R_1$ and $R_2$ are independently $C_{12}$ or $C_{14}$-alkyl; and
X is a halogen such as Cl, Br or I;
in the weight ratio of about
  25% of the compound where both $R_1$ and $R_2$ are $C_{12}$-alkyl;
  50% of the compound where $R_1$ is $C_{12}$-alkyl and $R_2$ is $C_{14}$-alkyl; and
  25% of the compound where both $R_1$ and $R_2$ are $C_{14}$-alkyl;
the stated weight percents being ±20%; and (b) a copolymer of vinylpyrrolidone and an acrylamido or vinyl quaternary ammonium monomer coprecipitated or in admixture with (a).

In the preferred embodiment of the invention, Z in the formula is $-(CH_2CH_2O)_n-$ and n is 2; and the monomer is an acrylamido quaternary ammonium monomer.

These compositions exhibit excellent antibacterial activity, low toxicity, water solubility and a low irritation effect on the skin of the user.

DETAILED DESCRIPTION OF THE INVENTION

1. Preparation of Blend Compositions

The several bis-quaternary ammonium compounds which comprise the blend composition (a) are made by reacting one mole of a selected dihalo compound selected from

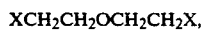

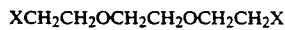

and

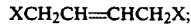

where X is a halide such as Cl, Br and I, with 2 moles of dodecyldimethyl amine, tetradecyldimethylamine or predetermined mixtures thereof.

A typical reaction is the following:

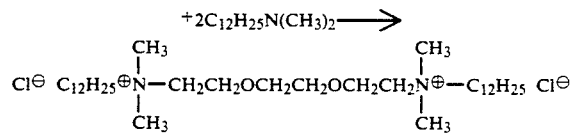

Accordingly, a reaction mixture of one mole of dodecyldimethylamine, one mole of the tetradecyldimethylamine and one mole of the selected dichloro compound will provide the following blend compositions:

BLEND COMPOSITION D

Compound A

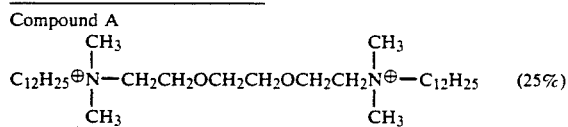

Compound B

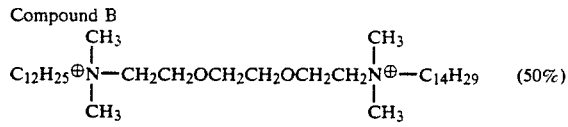

Compound C

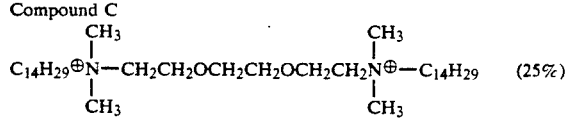

BLEND COMPOSITION H

Compound A'

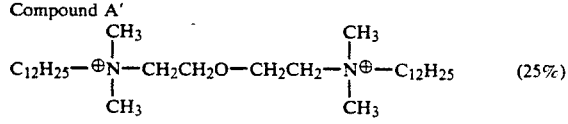

Compound B'

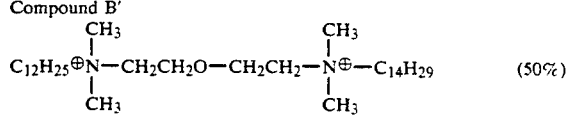

-continued

Compound C'

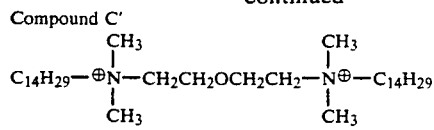     (25%)

BLEND COMPOSITION L
Compound A"

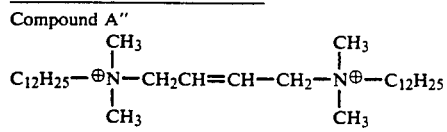     (25%)

Compound B"

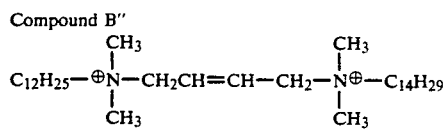     (50%)

Compound C"

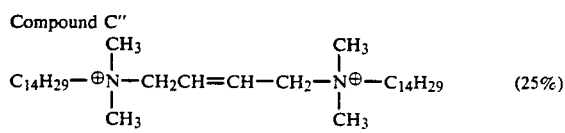     (25%)

where the stated percentages are ±20%; of course, by varying the relative amounts of starting materials, a blend of different percentages of the individual compounds may be obtained.

Another way of introducing the quaternary nitrogen into the polymer structure is by using monomers with functionality, either tertiary amine or reactive alkylating groups which are quaternizable.

2. Preparation of Copolymers of Vinylpyrrolidone and Acrylamido or Vinyl Quaternary Ammonium Monomer The following vinyl ammonium monomers can be copolymerized with vinyl pyrrolidone by solution polymerization in isopropyl alcohol or by precipitation polymerization in cyclohexane or heptane and under conditions to provide low molecular weight copolymers, i.e. about 10,000 to about 20,000, suitable for coprecipitation or admixture with the blend of bis-quaternary ammonium compounds.

Methacrylamidopropyl
Trimethylammonium Chloride (MAPTAC)

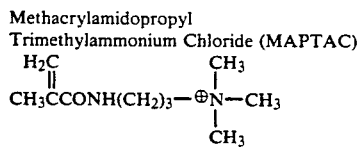     Cl⁻

Dodecyldimethylammonium Propyl
Methacrylamide Bromide or Iodide Salts

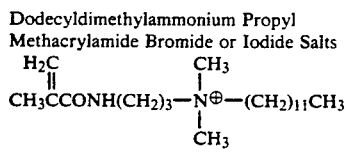     I⁻/Br⁻

Dodecyldimethylammonium Propyl
Acrylamide Bromide or Iodide Salts

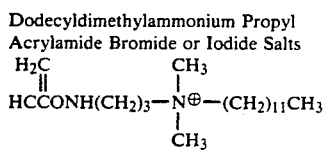     I⁻/Br⁻

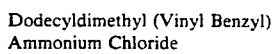

-continued

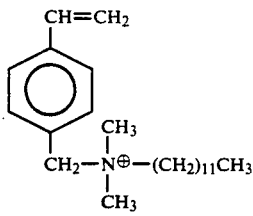     Cl⁻

Didecylmethyl (Vinyl Benzyl)
Ammonium Chloride

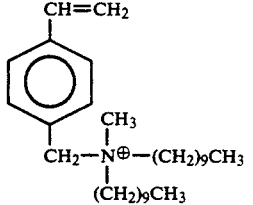     Cl⁻

A preferred copolymer is the copolymer of vinylpyrrolidone and MAPTAC, which is known as GAFQUAT ® HS-100 resin (ISP), and is supplied as a 20% aqueous solution.

The coprecipitate product comprising the blend composition and copolymer usually is prepared by reacting predetermined amounts of a dilute aqueous solution of the blend composition and copolymer, usually from 90:10 to 10:90 wt. ratio of each, respectfully, and removing the solvent. The desired coprecipitate is formed as a solid product.

These products exhibit an enhanced antimicrobial activity and reduced toxicity as compared to the individual compounds of the blend composition. Furthermore, they show excellent solubility in water, low toxicity and little irritation for the user.

The antimicrobial compositions of the invention may be used as such; however, preferably they are admixed with inert materials as pharmaceutical and cosmetic formulations, e.g. in the form of powders, solutions, lotions, suspensions and the like. Typical inert additives include water, alcohols, starch, and the like. Active ingredients also may be included in the product, if desired.

While the coprecipitate form of the antibacterial product of the invention is favored, admixtures of the blend and copolymer also may be used to prepare commercial compositions.

The antimicrobial activity of the products herein are represented by their Minimum Inhibitory Concentration (MIC) against E.Coli, a Gram negative microorganism. Their effect on skin is indicated by an Irritation Index. These properties are presented in the Table below for the individual compounds in blend D and the invention composition of several D, H and L blend compositions coprecipitated in a 50:50 wt. ratio with with GAFQUAT ® HS-100.

TABLE 1

| Compound/Composition | MIC | Irritation Index* |
|---|---|---|
| A compound in D blend | 100 | |
| B compound in D blend | 50 | |
| C compound in D blend | 125 | |
| D blend of 25A/50B/25C coprecipitated with GAFQUAT ® HS-100 (50:50) | 10 | 1 |
| D blend of 40A/20B/40C coprecipitated with | 20 | |

TABLE 1-continued

| Compound/Composition | MIC | Irritation Index* |
|---|---|---|
| GAFQUAT ® HS-100 (50:50) D blend of 33A/33B/33C coprecipitated with GAFQUAT ® HS-100 (50:50) | 20 | |
| D blend of 10A/80B/10C coprecipitated with GAFQUAT ® HS-100 (50:50) | 20 | |
| H blend of 25A'/50B'/25C' coprecipitated with GAFQUAT ® HS-100 (50:50) | 30 | 3 |
| L blend of 25A"/50B"/25C" coprecipitated with GAFQUAT ® HS-100 (50:50) | 10 | 4 |

*redness of skin, 1000 ppm active in water, scale of 1 to 10, with 10 being most irritating The $LD_{50}$ toxicity (on rats) of the blend compositions, D, above, with the copolymer, are reduced by a factor of 5-20 as compared to the individual compounds in the blend, as shown in Table 2 below.

TABLE 2

| Compound/Composition | $LD_{50}$ (g/kg) |
|---|---|
| A compound in D blend | 0.30 |
| B compound in D blend | 0.70 |
| C compound in D blend | 0.95 |
| D blend of 25A/50B/25C coprecipitated with GAFQUAT ® HS-100 (50:50) | 5.75 |
| H blend of 25A/50B/25C coprecipitated with GAFQUAT ® HS-100 (50:50) | 5.25 |
| L blend of 25A/50B/25C coprecipitated with GAFQUAT ® HS-100 (50:50) | 6.25 |

Accordingly, the antibacterial activity of the compositions of the invention are up to 12.5 times more favorable than the individual compounds of the blend; the product containing the D blend shows only ⅛ to ¼ as much irritation to the skin as the H and L blend products, respectively; and the blends are 5-20 less toxic than the individual compounds in the blends.

EXAMPLE 1

Preparation of Bisquat Blend Composition

A reaction solution of:
1,2-bis(2-chloroethoxy) ethane 37.5 g., 0.2 mole;
Dodecyldimethylamine 42.6 g., 0.2 mole;
Tetradecyldimethylamine 48.4 g., 0.2 mole;
Potassium Iodide 5 g.; and
Methanol 200 g.,
was mixed well and heated to 90°-100° C. for 12 hours. Then the solvent was removed to give a heavy syrupy residue which was treated with acetone to precipitate out the bis-quats blend composition in a yield of at least 95%. The composition comprised 25% by weight of A, 50% by weight of B and 25% by weight of C, above as determined by GC and HPLC analytical methods.

EXAMPLE 2

Preparation of the Coprecipitate Product 90 g. of a 1% by weight aqueous solution of GAFQUAT ® HS-100 was mixed with 10 g. of the bis-quat blend of Example 1. Then water was removed under reduced pressure. A solid coprecipitate was formed which analyzed 10% by weight active bis-quat blend, and 50% by weight copolymer.

While the invention has been described with particular reference to certain embodiments thereof, it will be understood that changes and modifications may be made which are within the skill of the art. Accordingly, it is intended to be bound only by the following claims, in which:

What is claimed is:

1. An antimicrobial, non-irritating composition comprising
(a) a blend of bis-quaternary ammonium compounds having the formula:

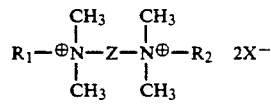

in which Z is $-(CH_2CH_2O)_nCH_2CH_2-$
where n is 1 or 2; or
$-CH_2CH=CH-CH_2-$; and
$R_1$ and $R_2$ are independently $C_{12}$ or $C_{14}$-alkyl; and
X is a halogen such as Cl, Br or I;
in the weight ratio of about
25% by weight of the compound where both $R_1$ and $R_2$ are $C_{12}$-alkyl;
50% by weight of the compound where $R_1$ is $C_{12}$-alkyl and $R_2$ is $C_{14}$-alkyl; and
25% by weight of the compound where both $R_1$ and $R_2$ are $C_{14}$-alkyl;
the stated weight percents being ±20%; and
(b) a low molecular weight copolymer of piolyvinylpyrrolidone and an acrylamido quaternary ammonium monomer selected from the group consisting of methacrylamidopropyl trimethylammonium chloride, dodecyldimethylammonium propyl methacrylamide bromide, dodecyldimethylammonium propyl methacrylamide iodide, docecyldimethylammonium propyl acrylamide bromide and dodecyldimethylammonium propyl acrylamide iodide, or a vinyl benzyl quaternary ammonium monomer selected from the group consisting of dodecyldimethyl (vinyl benzyl) ammonium chloride and didecylmethyl (vinyl benzyl) ammonium chloride wherein said copolymer is coprecipitated or in admixture with said blend in a weight ratio of 90:100 to 10:90 of each.

2. A composition according to claim 1 wherein Z is $-(CH_2CH_2O)_nCH_2CH_2-$.

3. A composition according to claim 2 wherein n is 2.

4. A composition according to claim 2 wherein n is 1.

5. A composition according to claim 1 wherein Z is $-CH_2CH=CH-CH_2-$.

6. A composition according to claim 1 where X is Cl or Br.

7. A composition according to claim 1 wherein said weight percentages are ±5-10%.

8. A composition according to claim 1 which includes an inert component.

9. A composition according to claim 1 wherein said copolymer is coprecipitated with the blend of bis-quaternary ammonium compounds.

10. A composition according to claim 1 wherein (a) and (b) are present in about a 50:50 wt. ratio.

11. A composition according to claim 1 wherein said acrylamido quaternary ammonium monomer is methacrylamidopropyl trimethylammonium chloride.

12. A composition according to claim 1 wherein said acrylamido quaternary ammonium monomer is dodecyldimethylammonium propyl methacrylamide bromide, dodecyldimethylammonium propyl methacrylate iodide, acrylamide bromide or acrylamide iodide.

13. A composition according to claim 1 wherein said vinyl benzyl quaternary ammonium monomer is dodecyldimethyl (vinylbenzyl) ammonium chloride.

14. A composition according to claim 1 wherein said vinyl benzyl quaternary ammonium monomer is didecylmethyl (vinylbenzyl) ammonium chloride.

* * * * *